(12) United States Patent
Liang (10) Patent No.: US 8,439,502 B2
(45) Date of Patent: May 14, 2013

(54) ALGORITHMS AND METHODS FOR DETERMINING ABERRATION-INDUCED VISION SYMPTOMS IN THE EYE FROM WAVE ABERRATION

(75) Inventor: Junzhong Liang, Fremont, CA (US)

(73) Assignee: Advanced Vision Engineering, Inc

( * ) Notice: Subject to any disclaimer, the term of this patent is extended or adjusted under 35 U.S.C. 154(b) by 0 days.

(21) Appl. No.: 11/371,288

(22) Filed: Mar. 8, 2006

(65) Prior Publication Data

US 2006/0203198 A1 Sep. 14, 2006

Related U.S. Application Data

(60) Provisional application No. 60/660,443, filed on Mar. 9, 2005.

(51) Int. Cl.
*A62B 3/00* (2006.01)
*A62B 3/10* (2006.01)

(52) U.S. Cl.
USPC .......................................... 351/246; 351/211

(58) Field of Classification Search .......... 351/205–223, 351/245, 246
See application file for complete search history.

(56) References Cited

U.S. PATENT DOCUMENTS

| | | | | |
|---|---|---|---|---|
| 6,827,444 B2* | 12/2004 | Williams et al. | ............... | 351/212 |
| 6,948,818 B2* | 9/2005 | Williams et al. | ............... | 351/211 |
| 7,077,522 B2* | 7/2006 | Williams | ..................... | 351/246 |

* cited by examiner

*Primary Examiner* — M. Hasan (57) ABSTRACT

Aberration-induced vision symptoms are determined by obtaining at least one wave aberration of an eye, calculating at least one point-spread function from the wave aberration, convolving the point-spread function of eye with at least one specially designed image for night vision diagnosis, and determining at least one aberration-induced vision symptom of the tested eye from the convolved images. The specially designed images are for vision diagnosis of aberration-induced glare, halo, ghost image, and starburst. The invention methods for specifying aberration-induced symptoms allow to find an optimized refractive corrections of defocus and astigmatism and to reduce vision symptoms caused by aberrations in the eye.

21 Claims, 7 Drawing Sheets

ALGORITHMS AND METHODS FOR DETERMINING ABERRATION-INDUCED VISION SYMPTOMS IN THE EYE FROM WAVE ABERRATION

CROSS-REFERENCES TO RELATED INVENTIONS

The present invention claims priority to the provisional U.S. patent application 60/660,443, titled "ALGORITHMS AND METHODS FOR THE PREDICTION OF NIGHT VISION SYMPTOMS" filed on Mar. 9, 2005 by Liang. The disclosures of these related applications are incorporated herein by reference.

TECHNICAL FIELD

This application relates to systems and methods for diagnosis of human vision, in particular, for determining aberration-induced vision symptoms in the eye from wave aberration.

BACKGROUND

Visual acuity has been the single most important parameter in measuring performance of human vision for over 150 years. Despite of its importance, visual acuity is almost useless for diagnosis of vision symptoms because it only measures vision performance with one specific task relating to visual resolution.

It is well-known that people can suffer from a host of night vision symptoms even though their visual acuity is 20/20 or better. This is particularly true for eyes after refractive surgeries. Surgical procedures can introduce unwanted high-order aberrations that are not correctable with conventional lenses.

Night vision symptoms are often referred as glare, halo, ghost images, and starburst. Even though night vision symptoms may not affect visual acuity, they can impair vision and make it dangerous for driving at night. It is unfortunate that vision of symptomatic eyes has never been properly cared because there is still no clinical means for specifying night vision symptoms.

Wavefront technology measures the total aberration in the eye including focus error, astigmatism, coma, spherical aberration, and a host of other high-order aberrations. It is often suspected that high-order aberrations contribute to most aberration-induced symptoms.

Figure 1:
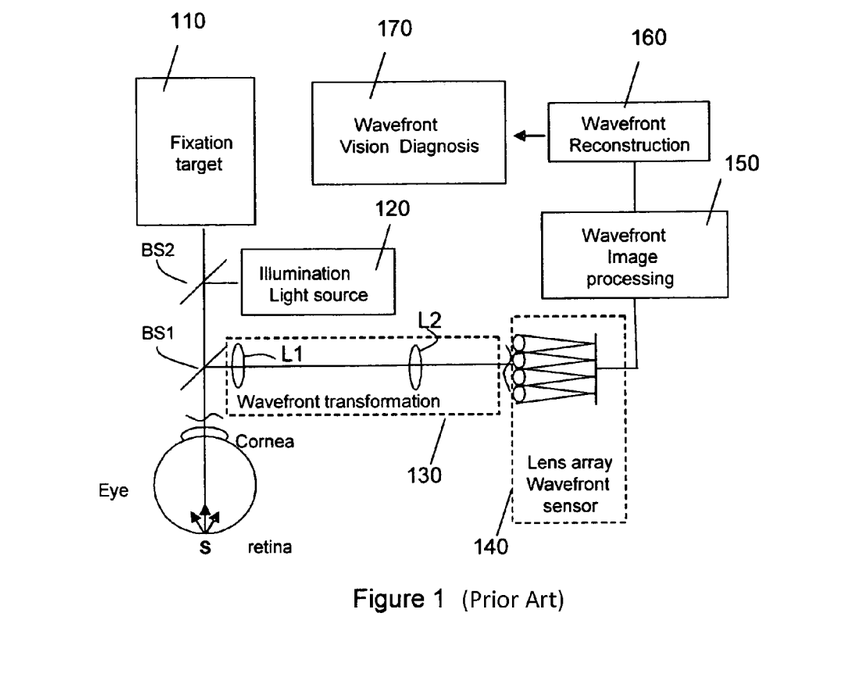
FIG. 1 shows a schematic diagram for a typical wavefront system for the eye using a Hartmann-Shack wavefront sensor.

FIG. 1 shows a schematic diagram for a typical wavefront system using a Hartmann-Shank wavefront sensor. (Aberrations in the eye can also be measured with other devices like the ray tracing aberrometers, the Talbot Interferometry based aberrometer, and the phase retrieval method.) A fixation system (110) assists the tested eye in stabilizing its accommodation and in maintaining the view direction. An illumination light source (120) generates a compact light source to reflect off mirror (BS2) and shine on the eye's retina as the probing light. The probing light is diffusely reflected by the retina, from which a distorted wavefront is formed at the eye's cornea plane. An optical relay system (130), consisting of lenses (L1) and (L2), relays the outgoing wavefront from the eye and reflected off of mirror BS1 to the plane of a lenslet array. A Hartmann-Shack wavefront sensor (140), consisting of a lenslet array and an image sensor, produces a wavefront sensor image as an array of focus spots. An image analysis module (150) detects the focus spots and calculates the wavefront slopes, from which the wavefront is reconstructed by a wavefront estimator (160). From the eye's wavefront aberration, a vision diagnosis module (170) provides qualification of the eye's optical defects as well as the eye's optical quality, which provides the basis for a vision correction diagnosis.

Specifying and determining night vision symptoms from aberrations in the eye has not been possible because of at least two fundamental issues. First, night vision symptoms are not clinically measurable so far and we have little information about the true nature of night vision symptoms. Second, aberrations are optical defects in the eye and there is a missing link between aberrations in the eye and true performance of human vision.

In light of the forgoing, it is readily apparent that a need exists in the art to provide methods to link vision symptoms to image blurs caused by aberrations, to make vision symptoms measurable with specifically-designed vision tests, and to reduce vision symptoms by changing the total aberrations in the eye.

SUMMARY

Implementations of the method may include one or more of the following. In one aspect, the present invention relates to a method for determining aberration-induced vision symptoms of an eye, comprising:

obtaining at least one wave aberration of an eye;

calculating at least one point-spread function from the wave aberration;

convolving the point-spread function of eye with at least one specially designed image for night vision diagnosis;

determining at least one aberration-induced vision symptom of the tested eye from the convolved images.

In a further aspect, the present invention includes specially designed vision testes for aberration-induced glare, halo, ghost image, and starburst.

In another aspect, the present invention relates to a method for determining an optimized refractive correction from a known wave aberration in the eye, with which aberration-induced vision symptoms is reduced.

In an additional aspect, the present invention relates to a method for reducing aberration-induced vision symptoms in the eye subjectively by selecting an optimized conventional sphero-cylindrical refractive correction.

Embodiments may include one or more of the following advantages. The invention methods provided effective means for demonstrating aberration-induced symptoms from the wave aberration in the eye for the first time. They can be used not only for diagnosis of vision symptoms but also for vision optimization for reduced symptoms in the eye. The invention methods add an additional dimension to vision care, can be used for objective assessments of night vision for drivers, for the selection of specific groups of people like pilots based on the night vision performance, for screening abnormal eyes suitable for wavefront-guided treatments, and for measuring the benefits of wavefront-guide treatment with spectacles, contact lenses, refractive surgeries, cataract surgeries.

DRAWING DESCRIPTIONS

FIG. 4 shows the point-spread functions in an ideal, aberration-free eye for three pupil sizes and the corresponding retinal images of the test object for glare and halo shown in FIG. 2a.

DETAILED DESCRIPTION OF THE INVENTION

Glare is often caused by light scattering in the eye, but can also be caused by significant uncorrected aberrations. Glare caused by light scattering are due to scattering centers on a microscopic scale whereas aberration-induced glare are caused by aberrations, being optical defects over an optical zone in mm scale.

Glare caused by light scattering happens in every eye and has impact on vision for a large view angle (at least a few degrees). Conventional methods for measuring glare in the eye are designed for glare caused by light scattering in a large viewing angle (>1 degree) in the eye. They are not suitable for measuring aberration-induced glare and halo because aberration-induced image blur is concentrated within a much narrower viewing angle (less than 1 degree).

Figures 2, 2A, 2B, 2C:
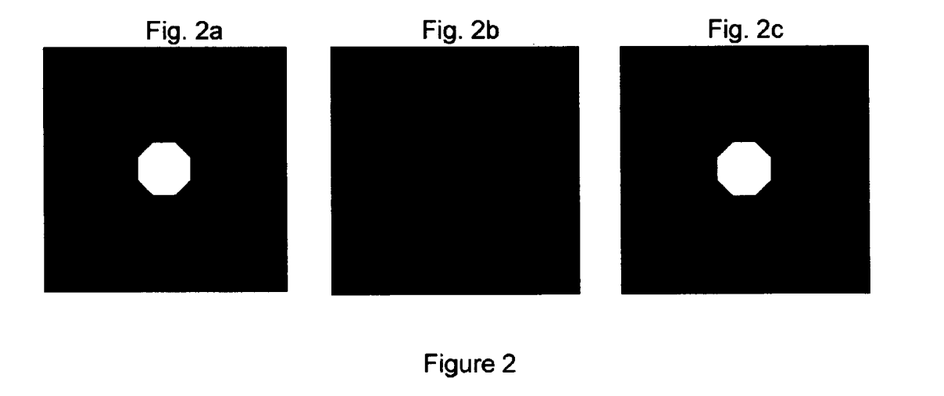
FIG. 2 shows a preferred embodiment of test objects specifically designed for diagnosis of glare and halo in accordance with the present invention.

Glare and halo are vision symptoms caused by nearby bright light sources. We propose a specially-designed vision test for aberration-induced glare and halo as shown in FIG. 2. Aberration-induced glare and halo can be tested clinically and predicted using optical simulation using this new vision object.

A preferred embodiment for the test object, shown in FIG. 2a, contains a bright extended Glare Source (GS) at the center and a dim Glare Target (GT) surrounding the glare source. A preferred embodiment of the glare source is shown in FIG. 2c. It is an extended pattern (a polygon shape) with uniform intensity. A preferred embodiment of the Glare Target (GT), shown in FIG. 2b, contains letters arranged in several radial distances from the center: the single-digit numbers at the first distance, letters at the second distance, and two-digit numbers at the $3^{rd}$ radial distance. The brightness of the Glare Target (GT) is much lower compared to the Glare Source (GS).

The intensity profile of the glare chart (O) can be represented as the sum of the glare source (G) and the glare target (T), i.e., $$O = G + k*T. \quad [1]$$

The intensity of the glare source is unity whereas the relative intensity of the glare target is k, much smaller than 1.

The retinal image of the glare chart, represented by O', can be simulated by convolving the glare chart (O) with the eye's point spread function (H), i.e., $$O' = (G + k*T) \otimes H, \quad [2a]$$

Where $\otimes$ is a convolution operator. Light spread from the bright glare source (G) can cause vision disturbance in the area with the dim glare target.

Figure 3:
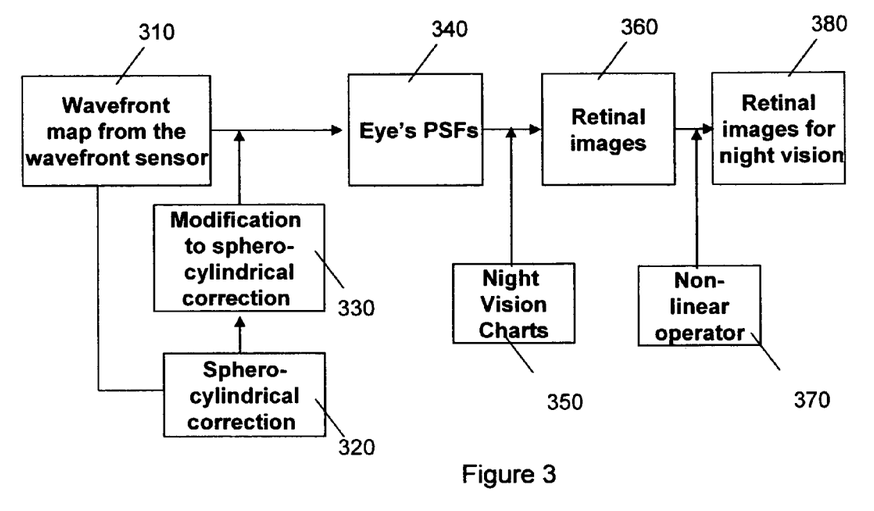
FIG. 3 shows the block diagram of a method for determining vision symptoms from wave aberration in the eye in accordance with the present invention.

FIG. 3 shows the block diagram for the simulation of night vision symptoms. The process may contain the following steps. First, wave aberration of the eye is obtained from a wavefront device (310). Second, the wavefront from the wavefront sensors is modified by including a sphero-cylindrical correction (320). Modification to the sphero-cylindrical correction is also included for the determination of best sphero-cylindrical correction, or for real eyes whose sphero-cylindrical error is not fully corrected. Third, the eye's point-spread functions at multiple pupil sizes (340) are calculated from the wave aberration in the eye. Fourth, specific night vision targets (350) are introduced for the evaluation of glare, halo, starburst, or ghost images. Fifth, retinal images of the designed vision targets are derived by convolving the vision targets with the eye's point-spread function (360). Sixth, certain non-linear image processing operations (370) like gamma control, contrast enhancement and segmentation, may be applied to the retinal images. Finally, night vision symptoms are evaluated based on the retinal images (380).

For the effective demonstration of visual disturbance by the glare source, we can also chose to make the glare target unchanged by image blur while the glare source is blurred by eye's point-spread function. Hence, the simulated retinal images is $$O'' = G \otimes H + k*T \quad [2b]$$

Where G⊗H is the convolution of Glare Source (G) with the point-spread function of the eye (H). Light spread from the glare source will appear in the area of glare targets that may cause disturbance to the view of the glare targets.

Figures 4, 4A, 4B, 4C:
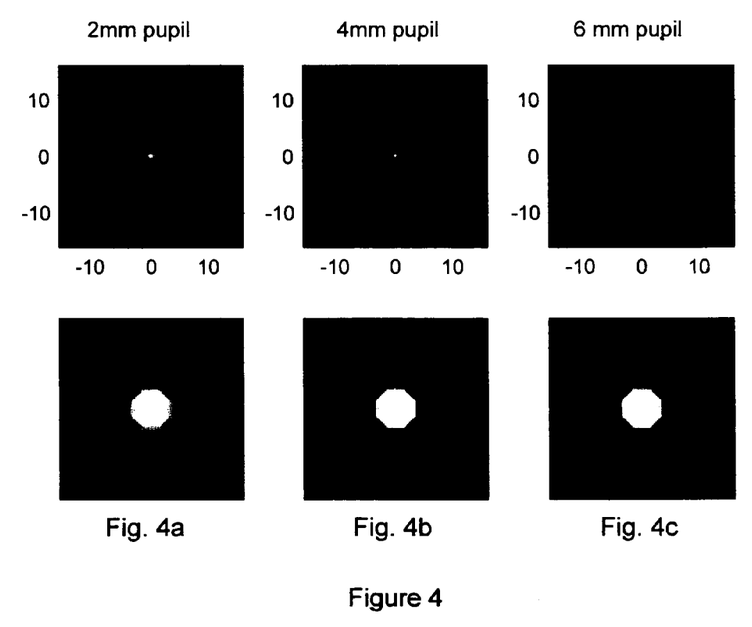

FIG. 4 shows the point-spread functions an ideal aberration-free eye for three pupil sizes and the retinal images of the test object for glare and halo shown in FIG. 2. On the top are the point-spread functions for pupil sizes of 2 mm, 4 mm and 6 mm, respectively. At the bottom are the corresponding retinal images showing that glare source is most blurred at the edge for the 2 mm pupil and least blurred for the 6 mm pupil. It confirms that image blur due to diffraction of light will not cause glare and halo for an aberration-free eye because Energy from the glare source has not impact in the region of glare targets.

Figure 5A:
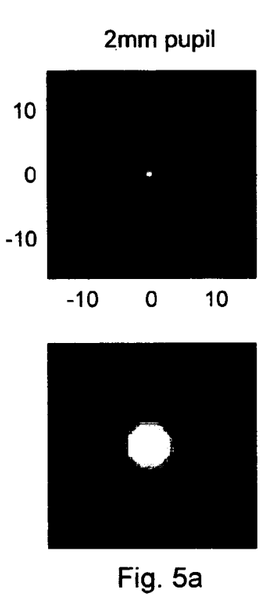
FIG. 5 shows the point-spread functions of an eye with horizontal coma of 0.3 microns in RMS (Root-Mean-Square) wavefront error for a 6 mm pupil, and demonstrates (directional) aberration-induced glare in the retinal image of the test object for glare and halo shown in FIG. 2a in a large 6 mm pupil.
Figure 5B:
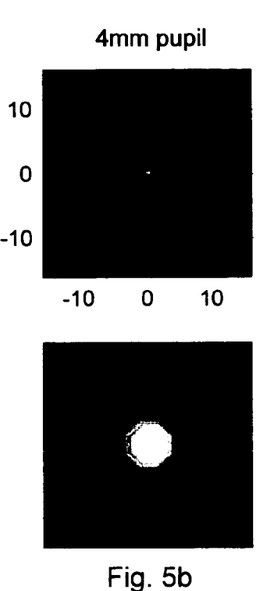
Figure 5C:
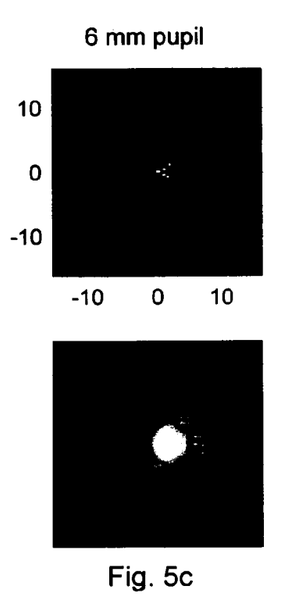

FIG. 5 shows the point-spread functions of an eye with a horizontal coma of 0.3 microns in RMS (Root-Mean-Square) wavefront error for a 6 mm pupil and (directional) aberration-induced glare in the retinal image of the test object for glare and halo shown in FIG. 2. One the top are the point-spread functions for pupil sizes of 2 mm, 4 mm and 6 mm, respectively. At the bottom are the corresponding retinal images showing that glare is negligible for 2 mm pupil (FIG. 5a) and for a 4 mm pupil (FIG. 5b), visible for the 6 mm pupil around 2, 3 and 4 at the first radial distance (FIG. 5c). The appearance of directional glare is related to the image blur by the point-spread function, but much apparent in the image blur of an extended glare source.

Figure 6A:
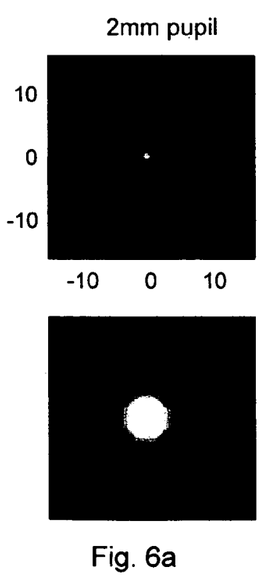
FIG. 6 shows the point-spread functions of an eye with a horizontal coma of 0.6 microns in RMS (Root-Mean-Square) wavefront error for a 6 mm pupil and a demonstration of (directional) aberration-induced glare in the retinal image of the test object for glare and halo shown in FIG. 2a in a large 6 mm pupil.
Figure 6B:
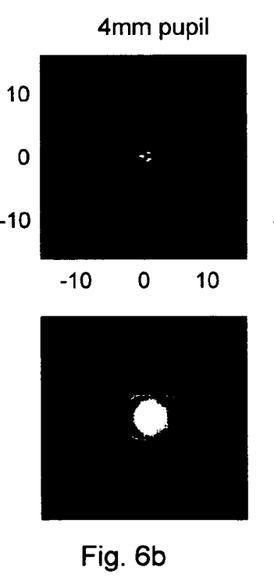
Figure 6C:
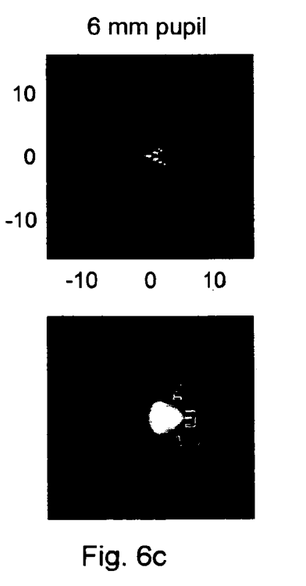

FIG. 6 shows the point-spread functions of an eye with a horizontal coma of 0.6 microns in RMS (Root-Mean-Square) wavefront error for a 6 mm pupil and (directional) aberration-induced glare in the retinal image of the test object for glare and halo shown in FIG. 2. One the top are the point-spread functions for pupil sizes of 2 mm, 4 mm and 6 mm, respectively. At the bottom are the corresponding retinal images showing that glare is negligible for 2 mm pupil (FIG. 6a), visible for a 4 mm pupil (FIG. 6b) around 2, 3 and 4 at the first radial distance, and significant for a 6 mm pupil (FIG. 6c) around 2, 3 and 4 reaching the third radial distance. The appearance of directional glare is related to the image blur by the point-spread function, but much apparent in the image blur of an extended glare source.

It is thus concluded that coma, which is not correctable with the conventional sphero-cylindrical correction, can spread the light from the glare source and cause glare in the eye. Impact of glare depends on the pupil size as well as the magnitude of comas.

Figures 7, 7B:
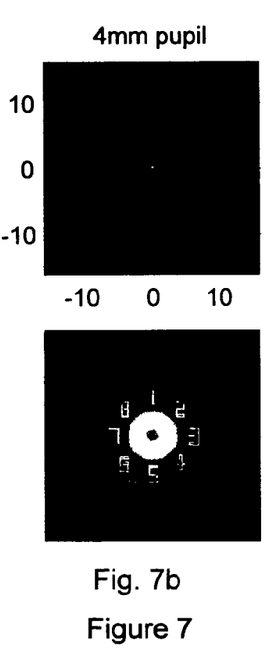
FIG. 7 shows the point-spread functions of an eye with spherical aberration of 0.6 microns in RMS (Root-Mean-Square) wavefront error for a 6 mm pupil and a demonstration of (symmetric) aberration-induced halo in the retinal image of the test object for glare and halo shown in FIG. 2. Spherically aberration in the eye is balanced with a focus correction for a minimized wavefront RMS.
Figure 7A:
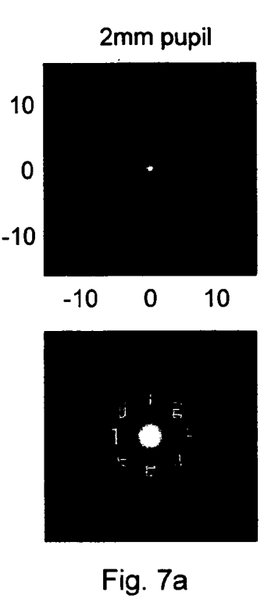
Figure 7C:
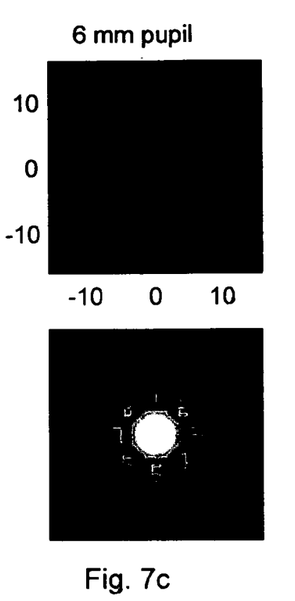

FIG. 7 shows the point-spread functions of an eye with spherical aberration of 0.6 microns in RMS (Root-Mean-Square) wavefront error for a 6 mm pupil and (symmetric) aberration-induced halo in the retinal image of the test object for glare and halo shown in FIG. 2. Spherically aberration in the eye is balanced with a focus correction to yield a minimized wavefront RMS. One the top are the point-spread functions for pupil sizes of 2 mm, 4 mm and 6 mm, respectively. At the bottom are the corresponding retinal images showing that halo is seen with spherical aberration in all directions at the first radial distance. Although the appearance of the three point-spread function are dramatic different for the three pupil sizes, halos are clearly seen in the image blur of the extended glare sources.

Figures 8, 8B:
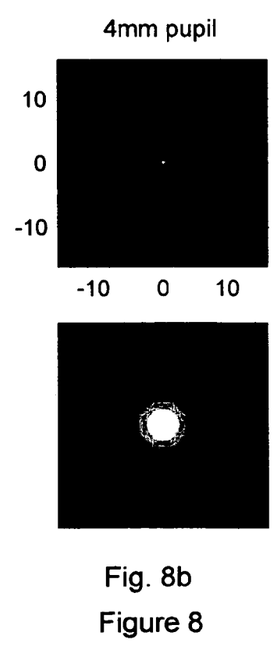
FIG. 8 shows the point-spread functions of an eye with spherical aberration of 0.6 microns in RMS (Root-Mean-Square) wavefront error for a 6 mm pupil and the retinal image of the test object for glare and halo shown in FIG. 2. Spherically aberration in the eye is balanced with an optimized focus correction for reduced vision symptoms.
Figure 8A:
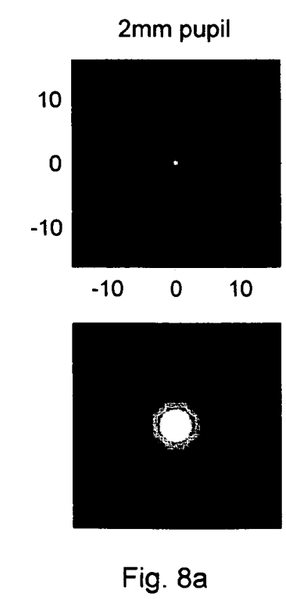
Figure 8C:
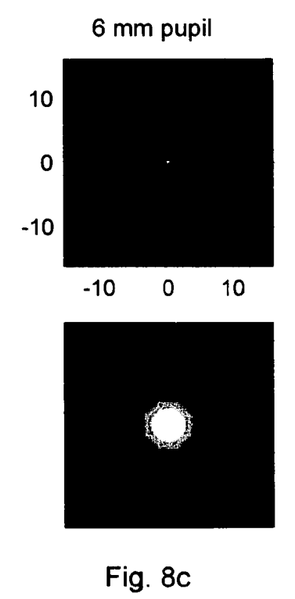

FIG. 8 shows the point-spread functions of an eye with spherical aberration of 0.6 microns in RMS (Root-Mean-Square) wavefront error for a 6 mm pupil and the retinal image of the test object for glare and halo shown in FIG. 2. Spherically aberration in the eye is balanced with an optimized focus correction to yield a minimized night vision halo. One the top are the point-spread functions for pupil sizes of 2 mm, 4 mm and 6 mm, respectively. At the bottom are the corresponding retinal images showing that no halo or glare is seen with proper correction of eye's sphero-cylindrical error.

The results in FIG. 7 and FIG. 8 demonstrate the importance of the best sphero-cylindrical correction when the eye has spherical aberration. It also indicates that our glare tests can be used for the determination of the best sphero-cylindrical correction by minimizing the night vision symptoms due to high order aberrations.

The test target shown in FIG. 2 can also be used to clinically measure the impact of glare and halo due to aberrations. A preferred embodiment is as follows. First, the glare target in FIG. 2b is presented to the patients without the glare source. The intensity of the glare target is adjusted to a threshold level so that the glare target is just visible or invisible without the glare source. Second, the glare source in FIG. 2c is introduced with the glare target. Light spread from the glare source will have impact on the appearance of the glare targets. Third, visual disturbance in the glare target by the glare source is reported by the patients. Fourth, vision diagnoses of glare and halo are obtained by comparing patients' descriptions and the simulated retinal images.

We have shown the methods for determining aberration-induced glare and halo with the test objects in FIG. 2. In order to determine other aberration-induced symptoms such as starburst and ghost images, additional vision tests must be designed.

Starburst is another type of night vision symptom appearing as a pattern of lines or light rays radiating outward from a center. It is often related to appearance of images of distant star-like objects. Starburst in normal eyes often has no practical significance because it relates mostly to distant star-like objects with which no vision tasks are critical.

Conventional starburst results from the combined effect of an eye's point-spread function and non-linear processing by the retina. We make distinction between the starburst in normal eyes that is retina-based for distant objects and in abnormal eyes that is optics-based for nearby objects. We define Optical Starburst as excessive image blur that produces starburst-like disturbance for nearby objects.

Figures 9, 9A, 9B:
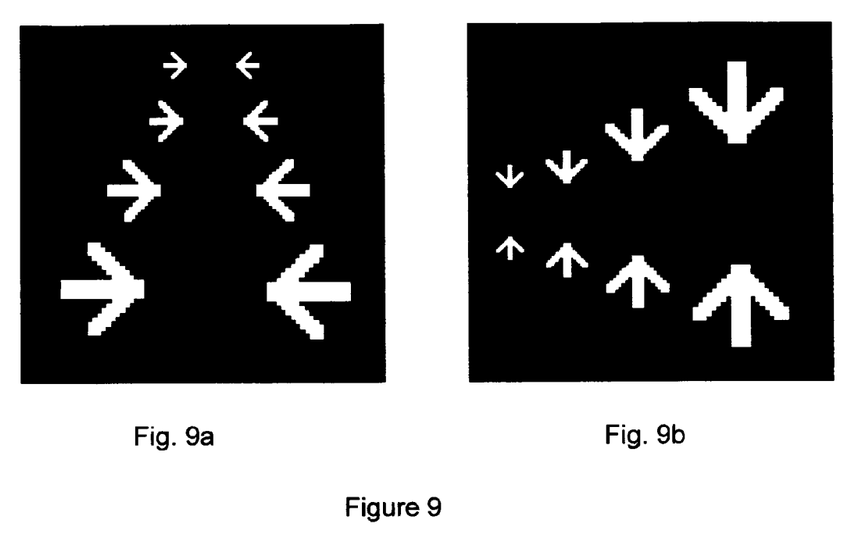
FIG. 9 shows a preferred embodiment of test objects specifically designed for the diagnosis of starburst and ghost images in accordance with the present invention.

For the simulation of optical starburst we propose to use a directional pattern such as an arrow-type target shown in FIG. 9. It has three fundamental features. First, it contains bright arrows with black background that is suited for the simulation of night vision. Second, horizontal and vertical arrows are selected because they are commonly used in traffic light designs. Third, arrows of different sizes are used for the representation of the objects at different distances.

The arrow-type target represents a category of night vision tasks that are sensitive to optical starburst. Variations to other types are also possible as long as they can be used to measure starburst-like disturbance for nearby objects.

When an eye's aberration is known, retinal images of arrow-type targets can be simulated by convolving the object with the eye's point-spread function. The same process in FIG. 3 can be used for the prediction of starburst and halo by using the arrow-type target in FIG. 9. FIG. 10 through FIG. 14 show the capability of night vision simulation with the arrow-type targets for optical starburst, halo and ghost images.

Figures 10, 10A, 10B, 10C:
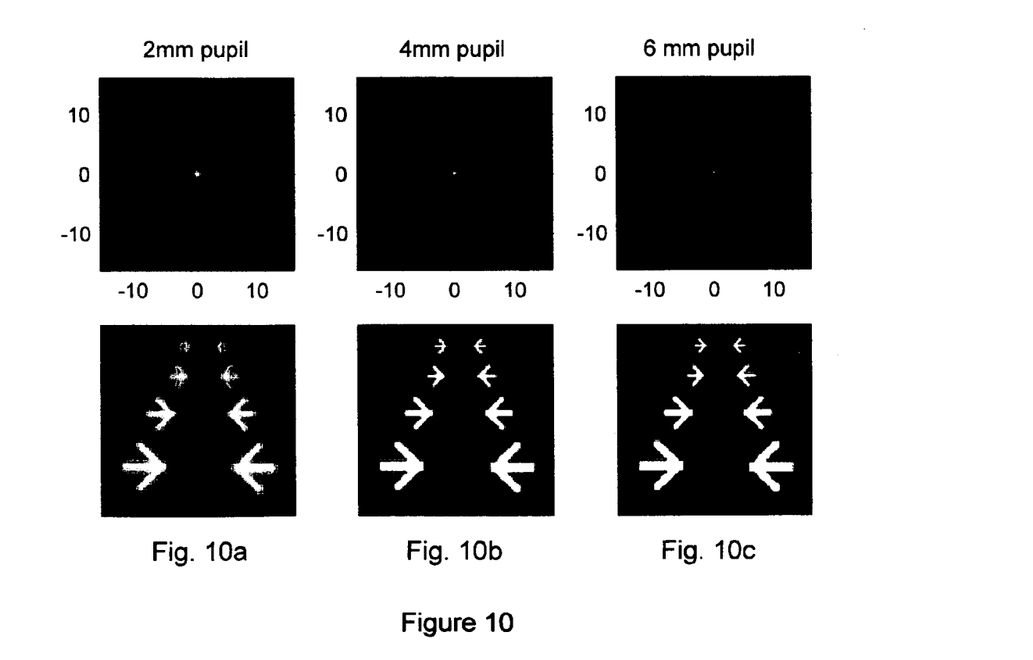
FIG. 10 shows the point-spread functions in an ideal aberration-free eye for three pupil sizes and the retinal images of the test object for starburst and ghost images shown in FIG. 9.

FIG. 10 shows the point-spread functions an ideal aberration-free eye for three pupil sizes and the retinal images of the test object for starburst and ghost images shown in FIG. 9. On the top are the point-spread functions for pupil sizes of 2 mm, 4 mm and 6 mm, respectively. At the bottom are the corresponding retinal images with image blur by diffraction only. It confirms that image blur caused by diffraction will not cause optical starburst, ghost image or halo in an aberration-free eye.

Figures 11, 11A, 11B, 11C:
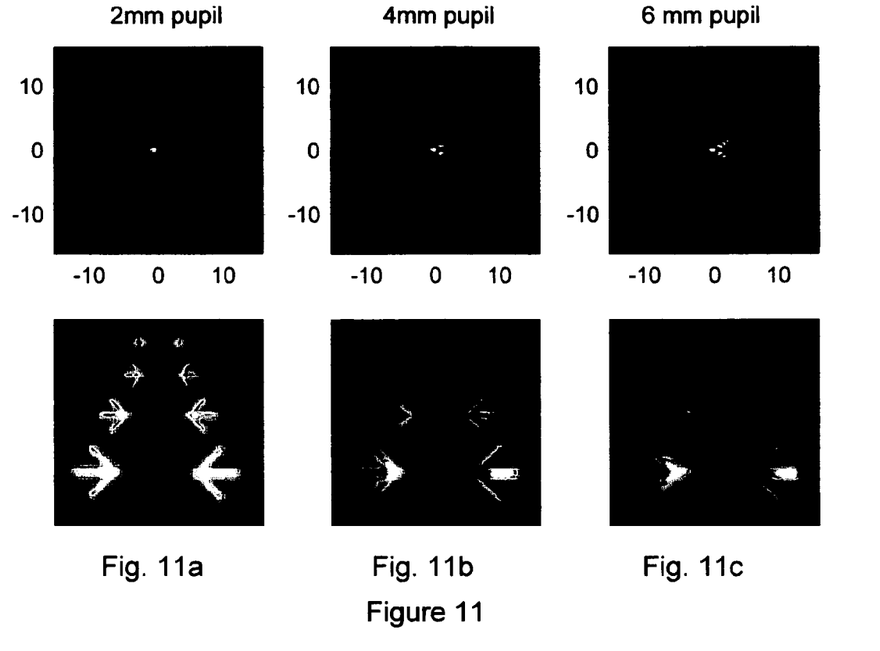
FIG. 11 shows the point-spread functions of an eye with a horizontal coma of 0.6 microns in RMS (Root-Mean-Square) wavefront error for a 6 mm pupil and aberration-induced starburst (right arrows) and ghost images (left arrows) in the retinal image of the test object for starburst and ghost images shown in FIG. 9 in a large 6 mm pupil.

FIG. 11 shows the point-spread functions of an eye with a horizontal coma of 0.6 microns in RMS (Root-Mean-Square) wavefront error for a 6 mm pupil and aberration-induced starburst and ghost images in the retinal image of the test object for starburst and ghost images shown in FIG. 9. On the top are the point-spread functions for pupil sizes of 2 mm, 4 mm and 6 mm, respectively. At the bottom are the corresponding retinal images showing that horizontal coma can cause optical starburst for the right arrows at 6 mm pupil and ghost images for the left arrows at 6 mm pupil.

Figures 12, 12A, 12B, 12C:
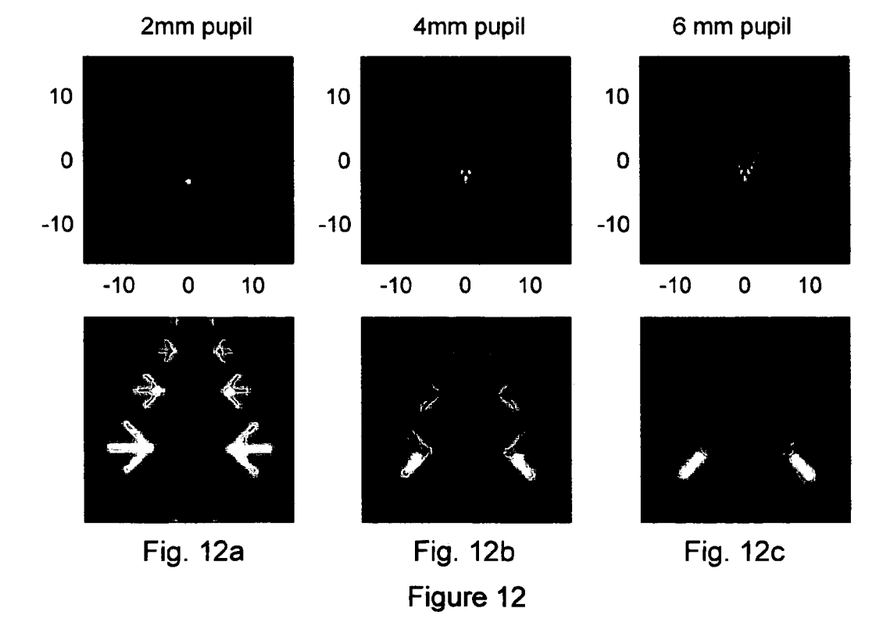
FIG. 12 shows the point-spread functions of an eye with a vertical coma of 0.6 microns in RMS (Root-Mean-Square) wavefront error for a 6 mm pupil and aberration-induced blurs in the retinal image of the test object for starburst and ghost images shown in FIG. 9.

FIG. 12 shows the point-spread functions of an eye with a vertical coma of 0.6 microns in RMS (Root-Mean-Square) wavefront error for a 6 mm pupil and aberration-induced blurs in the retinal image of the test object for starburst and ghost images shown in FIG. 9. On the top are the point-spread functions for pupil sizes of 2 mm, 4 mm and 6 mm, respectively. At the bottom are the corresponding retinal images for three pupil sizes. For the same scale of image blur, vertical coma will not cause starburst or ghost image for the horizontal arrows.

The results in FIG. 11 and FIG. 12 show that coma, which is not correctable by conventional sphero-cylindrical corrections, can cause optical starburst and ghost images that can impair night driving. It is also shown that the visual impact depends on the orientation of coma for a particular directional pattern.

Figures 13, 13B:
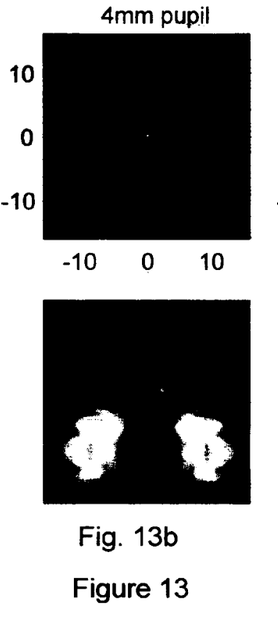
FIG. 13 shows the point-spread functions of an eye with spherical aberration of 0.6 microns in RMS (Root-Mean-Square) wavefront error for a 6 mm pupil and aberration-induced blurs in the retinal image of the test object for starburst and ghost images shown in FIG. 9. Spherically aberration in the eye is balanced with a focus correction to yield a minimized wavefront RMS.
Figure 13A:
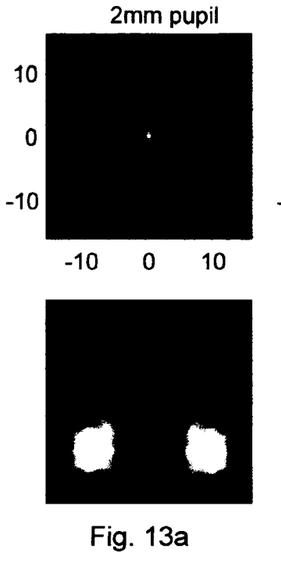
Figure 13C:
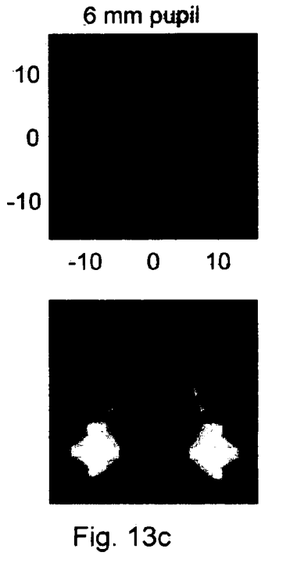

FIG. 13 shows the point-spread functions of an eye with spherical aberration of 0.6 microns in RMS (Root-Mean-Square) wavefront error for a 6 mm pupil and aberration-induced blurs in the retinal image of the test object for starburst and ghost images shown in FIG. 9. Spherically aberration in the eye is balanced with a focus correction to yield a minimized wavefront RMS. On the top are the point-spread functions for pupil sizes of 2 mm, 4 mm and 6 mm, respectively. At the bottom are the corresponding retinal images. It is seen that spherical aberration can cause halo and ghost images in the eye.

Figures 14, 14B:
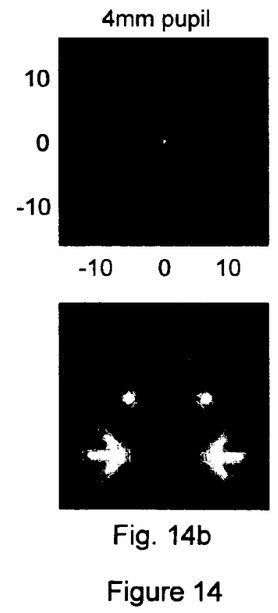
FIG. 14 shows the point-spread functions of an eye with spherical aberration of 0.6 microns in RMS (Root-Mean-Square) wavefront error for a 6 mm pupil and aberration-induced blurs in the retinal image of the test object for starburst and ghost images shown in FIG. 9. Spherically aberration in the eye is balanced with an optimized focus correction for minimized vision symptoms.
Figure 14A:
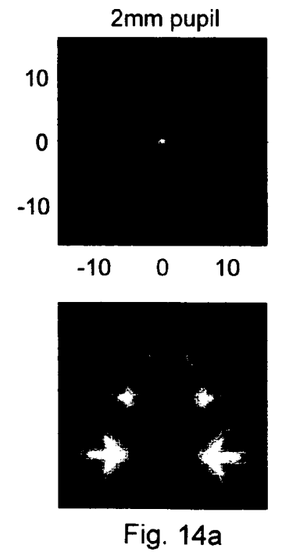
Figure 14C:
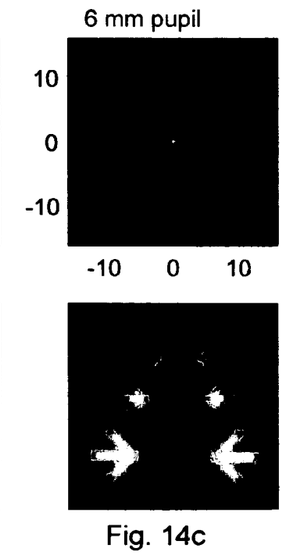

FIG. 14 shows the point-spread functions of an eye with spherical aberration of 0.6 microns in RMS (Root-Mean-Square) wavefront error for a 6 mm pupil and aberration-induced blurs in the retinal image of the test object for starburst and ghost images shown in FIG. 9. Spherically aberration in the eye is balanced with an optimized focus for minimal vision symptoms. On the top are the point-spread functions for pupil sizes of 2 mm, 4 mm and 6 mm, respectively. At the bottom are the corresponding retinal images showing that vision symptoms caused by spherical aberration can be reduced if a proper focus correction is selected.

The results in FIG. 13 indicate that spherical aberration, which is partially correctable by sphero-cylindrical correction, can cause halo, ghost image and starburst when the eye's focus error is not properly corrected. When the eye's focus is properly corrected, the impact of halo and starburst can be minimized as shown in FIG. 14. This demonstrates the importance of best sphero-cylindrical correction when the eye has significant spherical aberration. It also indicates that our arrow-type target can be used to determine the best sphero-cylindrical correction by minimizing the night vision symptoms due to high order aberrations.

The arrow-type target can also be used for the clinical assessment of night vision. We propose to test night vision with the arrow-type target at a number of light level and using multiple colors. A preferred process is as follows: First, the arrow-type vision chart is presented to a tested patient at one light level. The patient is asked to report smallest arrows readable without any problem. Second, the intensity of arrow-type object is adjusted to a different level, and the patient is asked again to report the smallest arrows readable at the new light level without any problem. Third, after testing vision at a number of different levels, the same vision test is performed at different colors like red, green and yellow. Finally, the performance of night vision with arrow-type targets at different light levels and with different colors can be used to for quantitative assessments of night vision.

A number of embodiments have been described. Nevertheless, it will be understood that various modifications may be made without departing from the spirit and scope of the invention. For example, advantageous results still could be achieved if steps of the disclosed techniques were performed in a different order and/or if components in the disclosed systems were combined in a different manner and/or replaced or supplemented by other components. Accordingly, other embodiments are within the scope of the following claims.

What is claimed is:

1. A method for specifying aberration-induced vision symptoms of an eye, comprising:
   obtaining at least one wave aberration of an eye;
   calculating at least one point-spread function from the wave aberration;
   calculating an image at a retina of an eye by convolving the calculated point-spread function with a specially designed image for night vision diagnosis, wherein the specially designed object comprises at least a bright extended Glare Source (GS) in a dark background or at least a directional pattern including an arrow in a dark background;
   displaying the calculated image at a retina of an eye and specifying aberration-induced glare as a directional light distribution outside the Glare Source area, aberration-induced halo as radially-symmetric light disturbance outside the Glare Source area, or aberration-induced ghost images as multiple images of the directional pattern.

2. The method of claim 1, wherein obtaining at least one wave aberration of an eye comprises measuring wave aberration of an eye with a wavefront aberrometer including but not limited to a Hartmann-Shack sensor based-aberrometer.

3. The method of claim 1, wherein a bright extended Glare Source (GS) in a dark background comprises at least a geometric pattern.

4. The method of claim 1, further comprises removing a refractive correction including focus error and astigmatism from the obtained wave aberration of an eye for the calculation of the point-spread function.

5. The method of claim 1, further comprises specifying a directional distribution of glare in at least one angle and specifying the glare strength in at least one radial distance.

6. The method of claim 1, further comprises specifying the halo strength in radial distances.

7. The method of claim 1, further comprises adding a dim Glare Target (GT) to the convolved image for an improved display of aberration induced glare and halo in the eye.

8. The method of claim 7, wherein the dim glare target (GT) comprises a pattern of features placed outside the Glare Source (GS) area and arranged at several radial distances and meridians from an center location in a black background.

9. A method for determining an optimized refractive correction for a minimized aberration-induced vision symptom in the eye, comprising:

measuring wave aberration of an eye with a wavefront aberrometer including but not limited to a Hartmann-Shack sensor based-aberrometer;

calculating a plurality of point-spread functions from the wave aberration under a plurality of refractive corrections;

convolving the point-spread functions with at least one specially designed image for night vision diagnosis;

specifying at least one aberration-induced vision symptom based on the convolved images of the eye;

selecting a refractive correction corresponding to a minimized aberration-induced vision symptoms.

10. The method of claim 9, wherein the specially designed image comprises at least a bright extended Glare Source (GS) in a dark background.

11. The method of claim 10, further comprises adding a dim Glare Target (GT) to the convolved image for an improved display of aberration induced glare and halo in the eye.

12. The method of claim 9, wherein the specially designed image comprises at least a directional pattern like an arrow in dark background.

13. The method of claim 12, wherein the directional pattern has different sizes corresponding to an object at different viewing distances.

14. The method of claim 9, wherein the aberration-induced vision symptoms include glare, halo, ghost image and starburst.

15. A method for reducing aberration-induced vision symptoms in the eye, comprising:

obtaining at least one wave aberration of an eye;

calculating a plurality of point-spread functions from the wave aberration under a plurality of refractive corrections;

convolving the point-spread functions with at least one specially designed image for night vision diagnosis;

specifying at least one aberration-induced vision symptom based on the convolved images of the eye under a refractive correction corresponding to a minimized vision symptom;

minimizing aberration induced symptoms by optimizing conventional sphero-cylindrical refractive correction subjectively using the specially designed image for night vision diagnosis, if the minimized vision symptom is within an acceptable level for normal eyes.

16. The method claim of 15, wherein obtaining at least one wave aberration of an eye comprises measuring wave aberration of an eye with a wavefront aberrometer including but not limited to a Hartmann-Shack sensor based-aberrometer.

17. The method of claim 15, wherein the specially designed image comprises at least a bright extended Glare Source (GS) in a dark background.

18. The method of claim 17, further comprises adding a dim Glare Target (GT) to the convolved image for an improved display of aberration induced glare and halo in the eye.

19. The method of claim 15, wherein the specially designed image comprises at least one directional pattern like an arrow in dark background.

20. The method of claim 19, wherein the directional pattern has different sizes corresponding to an object at different viewing distances.

21. The method of claim 15, wherein the aberration-induced vision symptoms includes glare, halo, ghost image and starburst.

\* \* \* \* \*

UNITED STATES PATENT AND TRADEMARK OFFICE
CERTIFICATE OF CORRECTION

PATENT NO.        : 8,439,502 B2
APPLICATION NO.   : 11/371288
DATED             : May 14, 2013
INVENTOR(S)       : Junzhong Liang It is certified that error appears in the above-identified patent and that said Letters Patent is hereby corrected as shown below:

On the Title page, at (73) Assignee:, please delete "Advanced Vision Engineering, Inc." and insert
--Perfect Vision Technology (HK) Ltd.--.

Signed and Sealed this
Tenth Day of September, 2013

Teresa Stanek Rea
*Acting Director of the United States Patent and Trademark Office*